United States Patent
Jung et al.

(10) Patent No.: US 10,176,568 B2
(45) Date of Patent: Jan. 8, 2019

(54) TOMOGRAPHIC APPARATUS AND METHOD

(71) Applicant: SAMSUNG ELECTRONICS CO., LTD., Suwon-si (KR)

(72) Inventors: Ji-young Jung, Bucheon-si (KR); Jong-hyon Yi, Yongin-si (KR); Min-kyu Sun, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 249 days.

(21) Appl. No.: 15/167,003

(22) Filed: May 27, 2016

(65) Prior Publication Data

US 2016/0350916 A1 Dec. 1, 2016

(51) Int. Cl.
| | |
|---|---|
| *G06K 9/00* | (2006.01) |
| *G06T 7/00* | (2017.01) |
| *G06T 11/00* | (2006.01) |
| *G06T 11/20* | (2006.01) |
| *A61B 6/03* | (2006.01) |
| *A61B 6/00* | (2006.01) |

(52) U.S. Cl.
CPC ............ *G06T 7/0012* (2013.01); *A61B 6/032* (2013.01); *A61B 6/481* (2013.01); *A61B 6/508* (2013.01); *A61B 6/54* (2013.01); *A61B 6/583* (2013.01); *G06T 11/003* (2013.01); *G06T 11/206* (2013.01); *G06T 2207/10016* (2013.01); *G06T 2207/10081* (2013.01)

(58) Field of Classification Search
None
See application file for complete search history.

(56) References Cited

U.S. PATENT DOCUMENTS

| 7,983,460 B2 | 7/2011 | Licato et al. | |
|---|---|---|---|
| 2004/0082846 A1* | 4/2004 | Johnson | ............ A61B 5/02014 600/410 |
| 2006/0247518 A1* | 11/2006 | Boing | .................... A61B 6/032 600/431 |
| 2010/0183206 A1* | 7/2010 | Carlsen | .................. A61B 6/032 382/128 |

* cited by examiner

*Primary Examiner* — Atiba O Fitzpatrick
(74) *Attorney, Agent, or Firm* — Sughrue Mion, PLLC

(57) ABSTRACT

A tomography apparatus includes an image processor configured to obtain a first image, which is a partial image of an object, by using data obtained from a first angle section corresponding to a first point, and to obtain a second image, which is a partial image of the object, by using data obtained from a second angle section corresponding to a second point subsequent to the first point; and a controller configured to obtain first information representing a brightness change, to obtain second information representing a rate of change in a Hounsfield unit (HU) value between the first point and the second point based on the first information, and to determine a tomography start point of the object based on the second information.

20 Claims, 13 Drawing Sheets

TOMOGRAPHIC APPARATUS AND METHOD

CROSS-REFERENCE TO RELATED APPLICATION

This application claims priority to Korean Patent Application No. 10-2015-0076486, filed on May 29, 2015, in the Korean Intellectual Property Office, the disclosure of which is incorporated herein in its entirety by reference.

BACKGROUND

1. Field

The exemplary embodiments disclosed herein relate to tomography methods and apparatuses, and more particularly, to tomography methods and apparatuses which may accurately predict a tomography start point in tomography which is performed by injecting contrast media.

2. Description of the Related Art

A medical imaging apparatus is equipment for obtaining an inner structure of an object in the form of an image. A medical image processor is a noninvasive test apparatus and captures images of structural details inside a body, an internal tissue, flow of fluid, etc., processes the images, and displays the images to a user. A user such as a doctor may diagnose a patient's health state and diseases by using a medical image output from the medical image processor.

A computed tomography (CT) apparatus may be a representative apparatus for capturing an image of an object by radiating X-rays to a patient.

Since a CT apparatus, which is a tomography apparatus among medical imaging processing apparatuses, may provide a cross-sectional image of an object, and is advantageous in that it is capable of expressing internal structures (for example, organs such as a kidney and a lung) of the object such that the internal structures do not overlap with each other compared with a general X-ray apparatus, the CT apparatus is widely used for accurate diagnosis of diseases. Hereinafter, a medical image obtained by the tomography apparatus is referred to as a cross-sectional image.

To obtain a cross-sectional image, tomography is performed on an object by using a CT apparatus, and raw data is obtained. Also, a cross-sectional image is reconstructed by using the obtained raw data. Here, the raw data may be projection data obtained by projecting an X-ray to an object, or a sinogram which is a set of projection data.

Tomography captures an image of an object by radiating X-rays to a patient. However, since X-rays used for tomography are a source of radioactivity, the X-ray has a disadvantage in that it is harmful to the human body.

As described above, since X-rays are harmful to the human body due to the radioactivity, a user needs to minimize an amount of radiation to which a patient including an object is exposed during an X-ray examination.

SUMMARY

Exemplary embodiments disclosed herein may provide tomography apparatuses and methods which may accurately predict a tomography start point by predicting a change in a Hounsfield unit (HU) value over time after injecting contrast media.

Exemplary embodiments disclosed herein may also provide tomography apparatuses and methods which may reduce a dose of X-rays radiated to an object by accurately predicting a tomography start point and starting tomography at the predicted point.

Additional aspects will be set forth in part in the description which follows and, in part, will be apparent from the description, or may be learned by practice of the presented exemplary embodiments.

According to an aspect of an exemplary embodiment, there is provided a tomography apparatus including: an image processor configured to perform tomography on an object to thereby obtain a first image, which is a partial image of the object, by using data obtained from a first angle section corresponding to a first point, and to obtain a second image, which is a partial image of the object, by using data obtained from a second angle section corresponding to a second point subsequent to the first point; and a controller configured to obtain first information representing a brightness change between a region of interest of the first image and a region of interest of the second image designating a same location of the object, to obtain second information representing a rate of change in a Hounsfield unit (HU) value between the first point and the second point based on the first information, and to determine a tomography start point of the object based on the second information.

The first angle section may be less than 180 degrees and the second angle section may be less than 180 degrees.

The image processor may be configured to reconstruct the first image, which is an incomplete image, by using raw data obtained from the first angle section, and reconstruct the second image, which is an incomplete image, by using raw data obtained from the second angle section.

The controller may be configured to predict a time required for reaching a target HU value based on the second information, and determine the tomography start point based on the predicted time.

The tomography apparatus may further include a user input device configured to receive the target HU value from a user.

The controller may be configured to determine a point at which the HU value is equal to or greater than a threshold value as the tomography start point based on the second information.

The controller may be configured to obtain the second information by mapping the first information to the HU value corresponding to the first information.

The tomography apparatus may further include: a storage device configured to store the first information and a lookup table including the HU value corresponding to the first information, wherein the controller is configured to map the first information to the HU value corresponding to the first information by using the lookup table stored in the storage device.

The tomography apparatus may further include: a display configured to display a user interface screen including a graph representing the rate of change in the HU value over time.

The image processor may be configured to obtain an initial image reconstructed by using raw data obtained from the tomography, and set a region of interest in the obtained initial image.

The image processor may be configured to set the region of interest of the first image and the region of interest of the second image based on a location of the region of interest set in the obtained initial image.

According to an aspect of another exemplary embodiment, there is provided a tomography apparatus including: an image processor configured to perform tomography on an object to obtain a plurality of partial images by using data obtained from a plurality of angle sections, the plurality of angle sections respectively corresponding to a plurality of successive points; and a controller configured to set a region of interest designating a same location of the object in each of the plurality of partial images, to obtain first information representing a change in brightness between the regions of interest of two partial images corresponding to two adjacent points from among the plurality of partial images, to obtain second information representing a rate of change in a Hounsfield unit (HU) value in a time section comprising the plurality of successive points based on the first information, and to determine a tomography start point of the object based on the second information.

According to an aspect of another exemplary embodiment, there is provided a tomography method including: performing tomography on an object; obtaining, by the performing of the tomography, a first image, which is a partial image of the object, by using data obtained from a first angle section corresponding to a first point, and obtaining, by the performing of the tomography, a second image, which is a partial image of the object, by using data obtained from a second angle section corresponding to a second point subsequent to the first point; obtaining first information representing a brightness change between a region of interest of the first image and a region of interest of the second image designating a same location of the object; obtaining second information representing a rate of change in a Hounsfield unit (HU) value between the first point and the second point based on the first information; and determining a tomography start point of the object based on the second information.

The first angle section may be less than 180 degrees and the second angle section may be less than 180 degrees.

The obtaining of the first image and the second image may include: reconstructing the first image, which is an incomplete image, by using raw data obtained from the first angle section, and reconstructing the second image, which is an incomplete image, by using raw data obtained from the second angle section.

The determining of the tomography start point may include: predicting a time required to reach a target HU value based on the second information; and determining the tomography start point based on the predicted time.

The tomography method may further include receiving the target HU value from a user.

The determining of the tomography start point may include: determining a point at which the HU value is equal to or greater than a threshold value as the tomography start point based on the second information.

The obtaining of the second information may include: mapping the first information to the HU value corresponding to the first information.

The mapping may include: mapping the first information to the HU value corresponding to the first information by using the first information and a lookup table comprising the HU value corresponding to the first information.

The tomography method may further include: displaying a user interface screen comprising a graph representing the rate of change in the HU value over time.

The tomography method may further include: obtaining an initial image reconstructed by using raw data obtained from the performing of the tomography, and setting a region of interest in the obtained initial image.

The setting of the region of interest may include: setting the region of interest of the first image and the region of interest of the second image based on a location of the region of interest set in the obtained initial image.

According to an aspect of another exemplary embodiment, there is provided a tomography method including: performing tomography on an object using an imaging device which rotates around the object along a rotation path; obtaining, by the performing of the tomography, a plurality of partial images by using data obtained from a plurality of angle sections of the rotation path, the plurality of angle sections respectively corresponding to a plurality of successive points; setting a region of interest designating a same location of the object in each of the plurality of partial images; obtaining first information representing a brightness change between regions of interests of two partial images corresponding to two adjacent points from among the plurality of partial images; obtaining second information representing a rate of change of a Hounsfield unit (HU) value in a time section comprising the plurality of successive points based on the first information; and determining a tomography start point of the object based on the second information.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
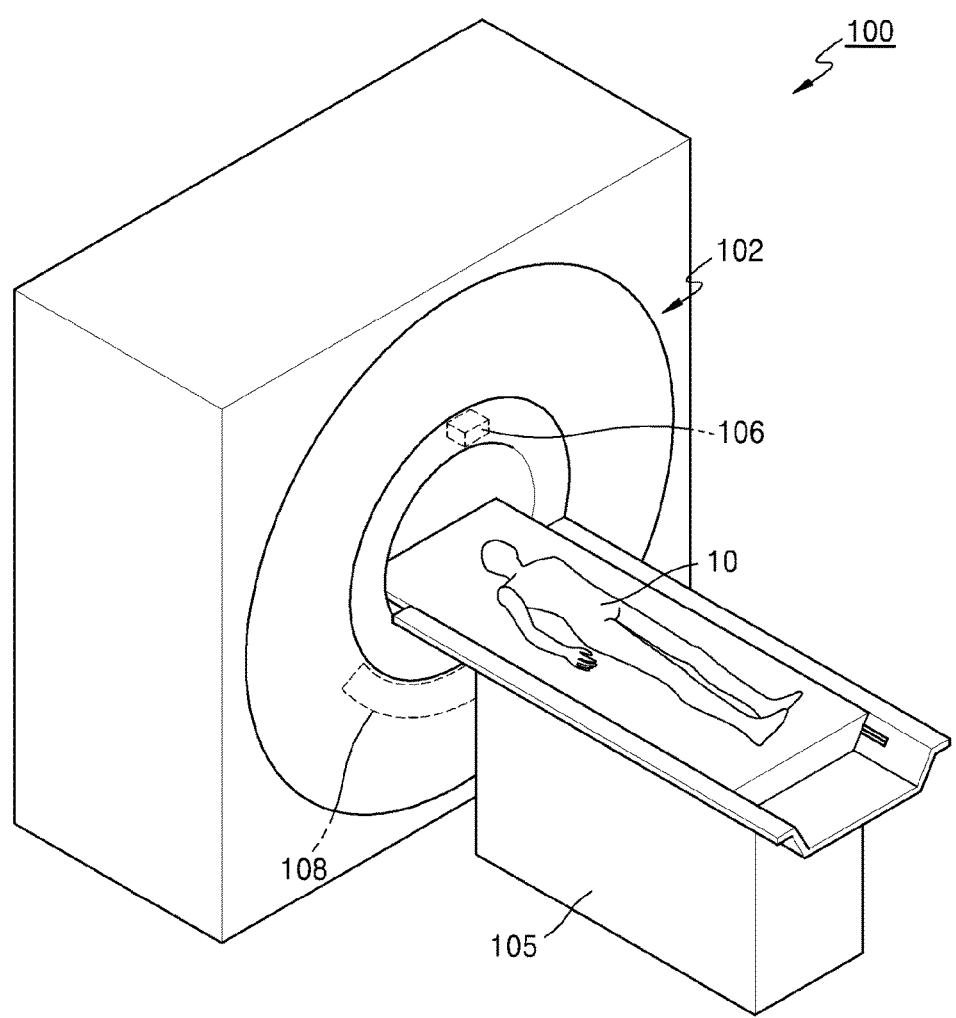
FIG. 1 is a schematic view illustrating a general computed tomography (CT) system.

The attached drawings for illustrating exemplary embodiments of the present disclosure are referred to in order to gain a sufficient understanding of the exemplary embodiments, the merits thereof, and the objectives accomplished by the exemplary embodiments. In this regard, the exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art, and the present exemplary embodiments will only be defined by the appended claims. Like reference numerals refer to like elements throughout the specification.

Hereinafter, the terms used in the specification will be briefly defined, and the exemplary embodiments will be described in detail.

The terms used in this specification are those general terms currently widely used in the art in consideration of functions regarding the exemplary embodiments, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the exemplary embodiments.

When a part "includes" or "comprises" an element, unless there is a particular description contrary thereto, the part can further include other elements, not excluding the other elements. Also, the term "unit" in the exemplary embodiments may refer to a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to exemplary embodiments, examples of which are illustrated in the accompanying drawings. In this regard, the present exemplary embodiments may have different forms and should not be construed as being limited to the descriptions set forth herein. In the following description, well-known functions or constructions are not described in detail so as not to obscure the exemplary embodiments with unnecessary detail.

Throughout the specification, an "image" may refer to multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

Throughout the specification, a "CT image" may refer to an image generated by synthesizing a plurality of X-ray images that are obtained by photographing an object while a CT imaging apparatus rotates around at least one axis with respect to the object.

Throughout the specification, an "object" may be a human, an animal, or a portion of a human or animal. For example, the object may be an organ (e.g., the liver, heart, womb, brain, breast, or abdomen), a blood vessel, or a combination thereof. The object may be a phantom. The phantom may refer to a material having a density, an effective atomic number, and a volume that are approximately the same as those of an organism. For example, the phantom may be a spherical phantom having properties similar to the physical body.

Throughout the specification, a "user" may be, but is not limited to, a medical expert including a medical doctor, a nurse, a medical laboratory technologist, a medial image expert, or a technician who repairs a medical apparatus.

Since a CT system is capable of providing a cross-sectional image of an object, the CT system may distinctively express an inner structure, e.g., an organ such as a kidney or a lung, of the object, compared to a general X-ray imaging apparatus.

The CT system may obtain a plurality of pieces of image data with a thickness not more than 2 mm several hundred times per second and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to allow a user to easily observe an area of interest in volume rendering.

Voxel of interest (VOI)—a method of displaying only a selected area in volume rendering.

A CT system 100 according to an exemplary embodiment will now be described with reference to FIGS. 1 and 2. The CT system 100 may include various types of devices.

FIG. 1 schematically illustrates the CT system 100. Referring to FIG. 1, the CT system 100 may include a gantry 102, a table 105, an X-ray generator 106, and an X-ray detector 108.

The gantry 102 may include the X-ray generator 106 and the X-ray detector 108.

An object 10 may be positioned on the table 105.

The table 105 may move in a predetermined direction (e.g., at least one of up, down, right, and left directions) during a CT imaging procedure. Also, the table 105 may tilt or rotate by a predetermined angle in a predetermined direction.

The gantry 102 may also tilt by a predetermined angle in a predetermined direction.

Figure 2:
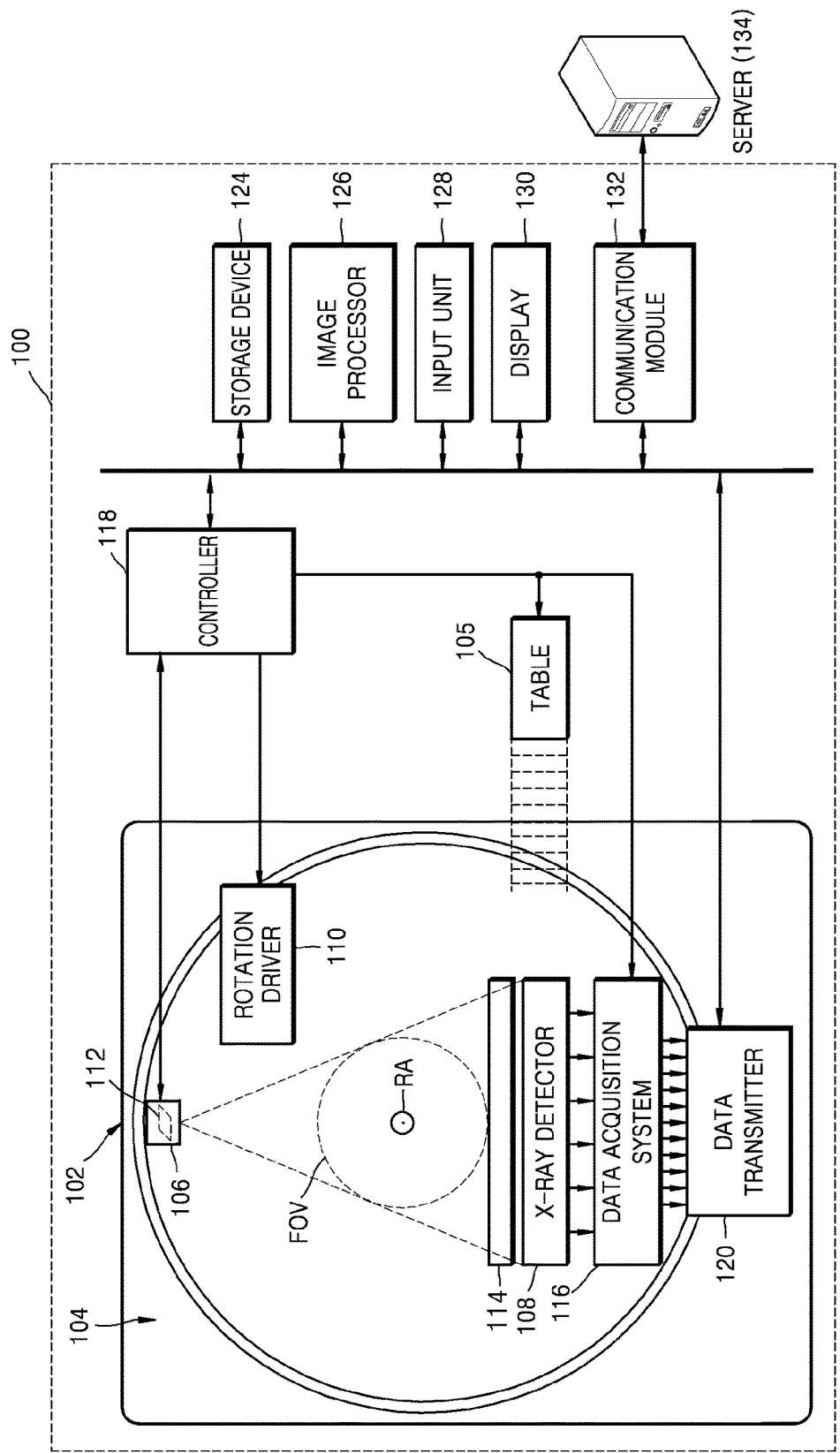
FIG. 2 is a diagram illustrating a structure of a CT system according to an exemplary embodiment.

FIG. 2 is a block diagram illustrating a structure of the CT system 100.

The CT system 100 may include the gantry 102, the table 105, a control unit 118 (e.g., controller), a storage device 124, an image processor 126, an input unit 128, a display unit 130 (e.g., display), and a communication module 132.

As described above, the object 10 may be positioned on the table 105. In the present exemplary embodiment, the table 105 may move in a predetermined direction (e.g., at least one of up, down, right, and left directions), and movement of the table 105 may be controlled by the control unit 118.

The gantry 102 may include a rotating frame 104, the X-ray generator 106, the X-ray detector 108, a rotation driver 110, a data acquisition system (DAS) 116, and a data transmitting unit 120.

The gantry 102 may include the rotating frame 104 having a loop shape capable of rotating with respect to a predetermined rotation axis RA. Also, the rotating frame 104 may have a disc shape.

The rotating frame 104 may include the X-ray generator 106 and the X-ray detector 108 that are arranged to face each other so as to have predetermined fields of view FOV. The rotating frame 104 may also include an anti-scatter grid 114. The anti-scatter grid 114 may be positioned between the X-ray generator 106 and the X-ray detector 108.

In a medical imaging system, X-ray radiation that reaches a detector (or a photosensitive film) includes not only attenuated primary radiation that forms a valuable image but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driver 110 and may rotate the X-ray generator 106 and the X-ray detector 108 at a predetermined rotation speed. The rotating frame 104 may receive the driving signal and power from the rotation driver 110 while the rotating frame 104 contacts the rotation driver 110 via a slip ring. Also, the rotating frame 104 may receive the driving signal and power from the rotation driver 110 via wireless communication.

The X-ray generator 106 may receive a voltage and current from a power distribution unit (PDU) via a slip ring and then a high voltage generating unit, and may generate and emit an X-ray. When the high voltage generating unit applies predetermined voltage (hereinafter, referred to as a tube voltage) to the X-ray generator 106, the X-ray generator 106 may generate X-rays having a plurality of energy spectra that correspond to the tube voltage.

The X-ray generated by the X-ray generator 106 may be emitted in a predetermined form due to a collimator 112.

The X-ray detector 108 may be positioned to face the X-ray generator 106. The X-ray detector 108 may be positioned to face the X-ray generator 106. Each of the plurality of X-ray detecting devices may establish one channel but one or more exemplary embodiments are not limited thereto.

The X-ray detector 108 may detect the X-ray that is generated by the X-ray generator 106 and that is transmitted through the object 10, and may generate an electrical signal corresponding to intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. Electrical signals generated by the X-ray detector 108 may be acquired by the DAS 116. Electrical signals generated by the X-ray detector 108 may be acquired by wire or wirelessly by the DAS 116. Also, the electrical signals generated by the X-ray detector 108 may be provided to an analog-to-digital converter via an amplifier.

According to a slice thickness or the number of slices, only some of a plurality of pieces of data collected by the X-ray detector 108 may be provided to the image processor 126 via the data transmitting unit 120, or the image processor 126 may select only some of the plurality of pieces of data.

Such a digital signal may be provided to the image processor 126 via the data transmitting unit 120. The digital signal may be provided to the image processor 126 by wire or wirelessly.

The control unit 118 may control an operation of each of the elements in the CT system 100. For example, the control unit 118 may control operations of the table 105, the rotation driver 110, the collimator 112, the DAS 116, the storage device 124, the image processor 126, the input unit 128, the display unit 130, the communication module 132, or the like.

The image processor 126 may receive data acquired by the DAS 116 (e.g., raw data that is data before processing), via the data transmitting unit 120, and may perform pre-processing.

The pre-processing may include, for example, a process of correcting a sensitivity irregularity between channels and a process of correcting signal loss due to a rapid decrease in signal strength or due to the presence of an X-ray absorbing material such as metal.

Data output from the image processor 126 may be referred to as raw data or projection data. The projection data may be stored in the storage device 124 with imaging conditions (e.g., the tube voltage, an imaging angle, etc.) during the acquisition of data.

The projection data may be a group of data values that correspond to the intensity of the X-ray that has passed through the object 10. For convenience of description, a group of a plurality of pieces of projection data that are simultaneously obtained from all channels at the same imaging angle is referred to as a projection data set.

The storage device 124 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processor 126 may reconstruct a cross-sectional image of the object 10 by using the acquired projection data set. The cross-sectional image may be a 3D image. In other words, the image processor 126 may reconstruct a 3D image of the object 10 by using a cone beam reconstruction method or the like, based on the acquired projection data set.

The input unit 128 may receive an external input with respect to an X-ray tomography imaging condition, an image processing condition, or the like. For example, the X-ray tomography imaging condition may include tube voltages, an energy value setting with respect to a plurality of X-rays, a selection of an imaging protocol, a selection of an image reconstruction method, a setting of an FOV area, the number of slices, a slice thickness, a parameter setting with respect to image post-processing, or the like. Also, the image processing condition may include a resolution of an image, an attenuation coefficient setting for the image, setting for an image combining ratio, or the like.

The input unit 128 may include a device for receiving a predetermined input from an external source For example, the input unit 128 may include a microphone, a keyboard, a mouse, a joystick, a touch pad, a touch pen, a voice recognition device, a gesture recognition device, or the like.

The display unit 130 may display an X-ray image reconstructed by the image processor 126.

Exchanges of data, power, or the like between the aforementioned elements may be performed by using at least one of wired communication, wireless communication, and optical communication.

The communication module 132 may perform communication with an external device, an external medical apparatus, etc., via a server 134 or the like. The communication will now be described with reference to FIG. 3.

Figure 3:
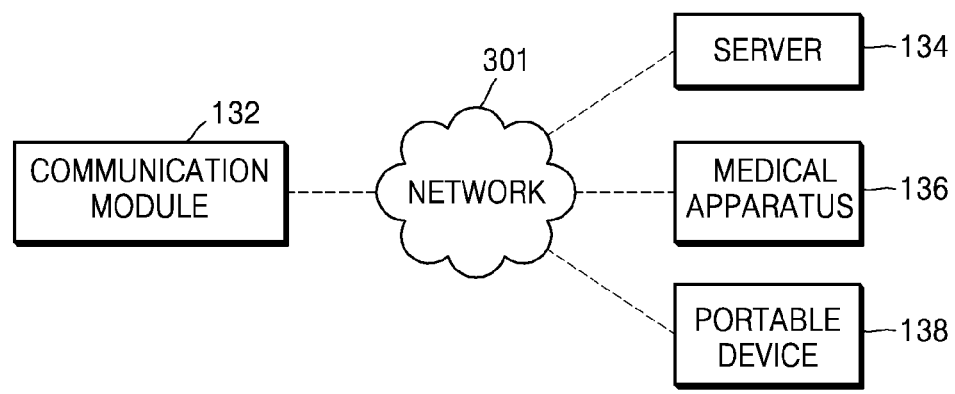
FIG. 3 is a block diagram illustrating communication performed by communication module.

FIG. 3 is a block diagram illustrating the communication performed by the communication module 132.

The communication module 132 may be connected by a wire or wirelessly connected to a network 301 and therefore may perform communication with the server 134, a medical apparatus 136, or a portable device 138. The communication module 132 may exchange data with a hospital server or other medical apparatuses in a hospital connected via a picture archiving and communication system (PACS).

Also, the communication module 132 may perform data communication with the portable device 138 or the like, according to the digital imaging and communications in medicine (DICOM) standard.

The communication module 132 may transmit and receive data related to diagnosing the object 10, via the network 301. Also, the communication module 132 may transmit and receive a medical image obtained from the medical apparatus 136 such as a magnetic resonance imaging (MRI) apparatus, an X-ray apparatus, or the like.

Furthermore, the communication module 132 may receive a diagnosis history or a medical treatment schedule about a patient from the server 134 and may use the diagnosis history or the medical treatment schedule to diagnose the patient. Also, the communication module 132 may perform data communication not only with the server 134 or the medical apparatus 136 in a hospital but also with the portable device 138 of a user or patient.

Also, the communication module 132 may transmit information about a device error, information about a quality control status, or the like to a system manager or a service manager via the network 301, and may receive a feedback regarding the information from the system manager or service manager.

As described with reference to FIGS. 1 to 3, the image processor 126 may reconstruct a cross-sectional image by using raw data (for example, projection data).

In reconstructing a cross-sectional image, reconstructing one cross-sectional image by using raw data obtained while the X-ray generator 106 makes one rotation is referred to as full reconstruction, and reconstructing one cross-sectional image by using raw data obtained while the X-ray generator 106 makes a half rotation or more and less than one rotation is referred to as a half reconstruction method.

Here, raw data may be projection data obtained by radiating radiation to an object, or a sinogram which is a set of projection data. Also, raw data may be an image generated by performing filtered backprojection on projection data or a sinogram. Specifically, when the X-ray generator 106 at a predetermined location emits an X-ray to an object, a point or a direction in which the X-ray generator 106 views the object is referred to as a view. Projection data denotes raw data obtained in response to one view, and a sinogram denotes raw data obtained by sequentially listing a plurality of projection data.

Figure 4A:
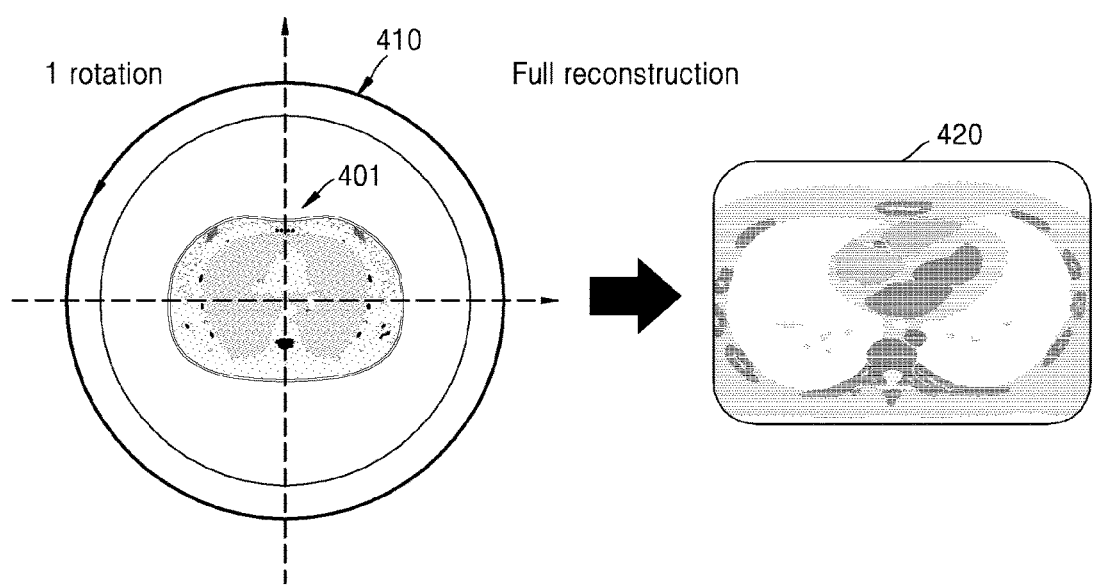
FIGS. 4A and 4B are diagrams for explaining a full reconstruction method and a half reconstruction method.
Figure 4B:
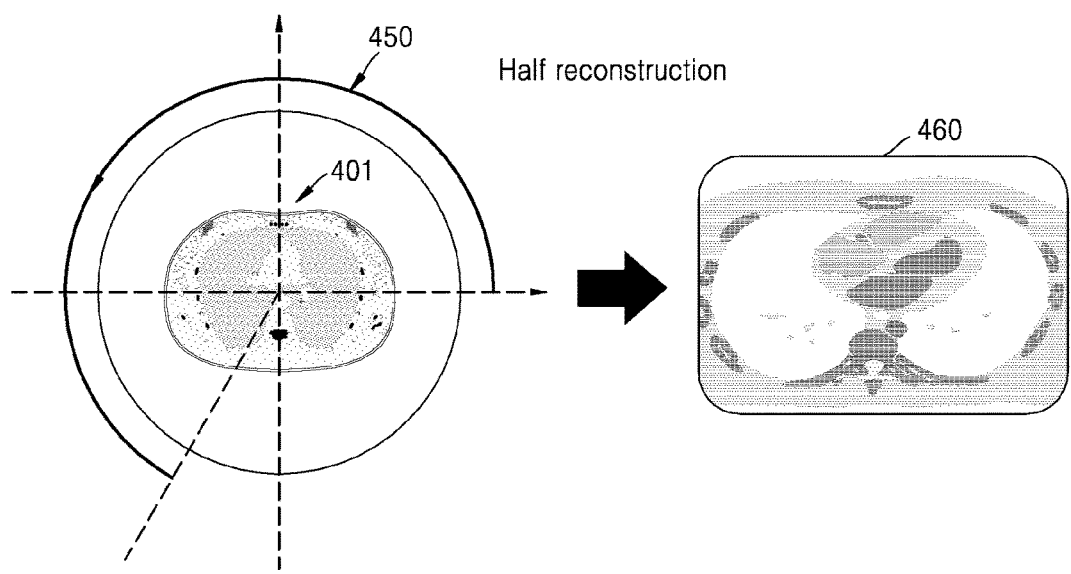

FIGS. 4A and 4B are diagrams for explaining a full reconstruction method and a half reconstruction method.

Here, FIG. 4A explains rotation of the X-ray generator 106 according to the full reconstruction method. In the full reconstruction method, the X-ray generator 106 performs tomography while making one rotation or more (410) around an object 401, and the image processor 126 may reconstruct a cross-sectional image 420 by using obtained raw data.

FIG. 4B explains rotation of the X-ray generator 106 according to the half reconstruction method. In the half reconstruction method, the X-ray generator 106 performs tomography while making rotation by 180 degrees or more (450) around the object 401, and the image processor 126 may reconstruct a cross-sectional image 460 by using obtained raw data.

A cross-sectional image reconstructed by the full reconstruction method or the half reconstruction method is a complete image entirely representing an object.

In an exemplary embodiment, to obtain an initial image, the full reconstruction method or the half reconstruction method may be used.

Figure 5:
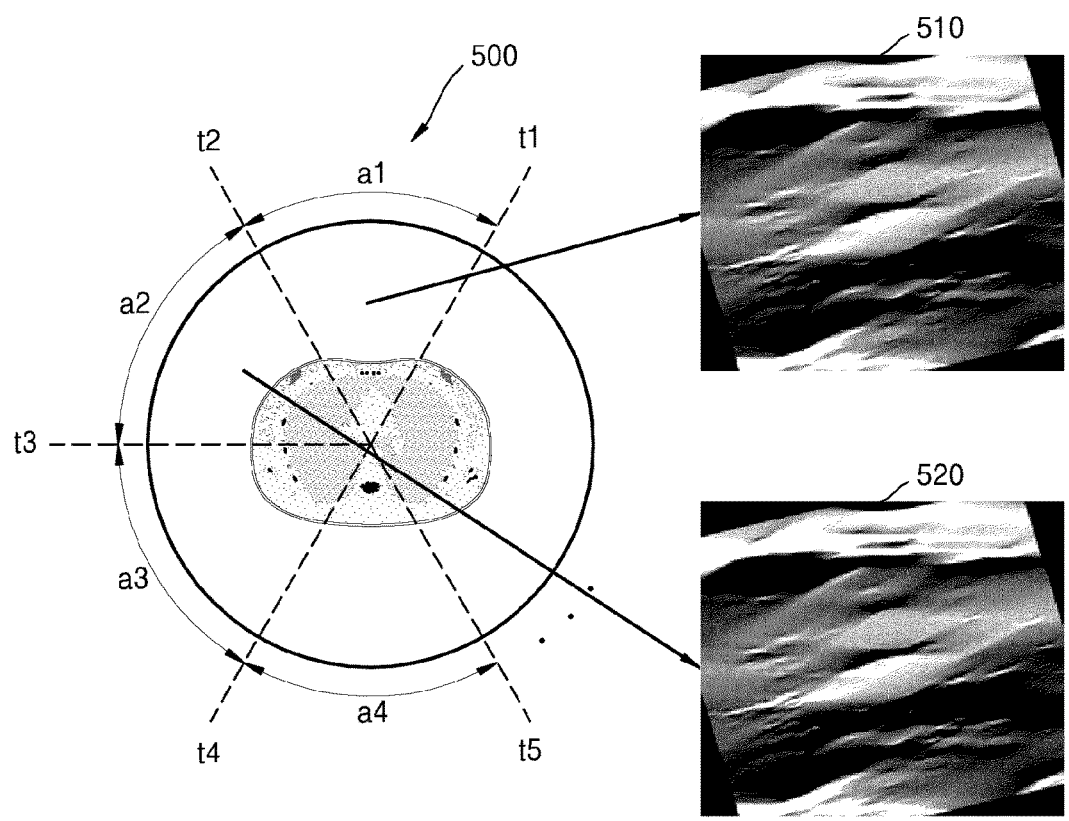
FIG. 5 is a diagram for explaining obtaining a partial image by using a partial angle reconstruction (PAR) method.

FIG. 5 is a diagram for explaining obtaining a partial image by using a partial angle reconstruction (PAR) method.

Reconstructing one cross-sectional image by using raw data obtained while the X-ray generator 106 makes less than a half rotation is referred to as the PAR method. A cross-sectional image reconstructed by the full reconstruction method or the half reconstruction method is a complete image entirely representing an object, but a cross-sectional image reconstructed by the PAR is an incomplete image partially representing an object. Here, an incomplete image reconstructed by the PAR may be referred to as a 'partial image' or a 'partial angle image'. Hereinafter, an image reconstructed by the PAR is referred to as a partial image.

Referring to FIG. 5, FIG. 500 shown in the left explains rotation of the X-ray generator 106 according to the PAR. The PAR reconstructs a cross-sectional image by using raw data obtained while the X-ray generator 106 makes less than a half rotation. For example, an angle section ranging from an angle t1 to an angle t2 may be referred to as "a1", an angle section ranging from an angle t2 to an angle t3 may be referred to as "a2", an angle section ranging from an angle t3 to an angle t4 may be referred to as "a3", and an angle section ranging from an angle t4 to an angle t5 may be referred to as "a4". Here, each of the angle sections "a1" to "a4" denotes a partial angle section included in one period angle section of less than one rotation. Specifically, the angle sections "a1" to "a4" may have a value less than 180 degrees.

The X-ray generator 106 may reconstruct a cross-sectional image from raw data obtained while making a rotation with respect to the angle sections "a1", "a2", "a3", and "a4". The reconstructed cross-sectional image is a partial image. A partial image 510 is a partial image reconstructed by using raw data obtained from the angle section "a1", and a partial image 520 is a partial image reconstructed by using raw data obtained from the angle section "a2".

In an exemplary embodiment, to obtain a first image, a second image, and a plurality of partial images, the PAR may be used.

In tomography, to allow a tissue or a blood vessel of an object to clearly appear, contrast media may be used. The contrast media absorb most of an X-ray, and a region in which a contrast enhancement effect is represented due to injection of contrast media is expressed as white. Therefore, accuracy of diagnosis may be raised by using contrast media and increasing a contrast degree between a tissue and a blood vessel of an object.

After the contrast media are injected, as time elapses, a contrast enhancement effect increases and an HU value increases. Therefore, to accurately diagnose an object via the tomography, a user should perform the tomography while a high contrast enhancement effect is maintained. However, since the contrast enhancement effect reduces again when a predetermined time elapses, to perform the tomography for a duration in which the contrast enhancement effect is maintained at a predetermined level or more, it is important to determine an accurate tomography start point.

In an exemplary embodiment, a change in an HU value may be tracked from an incomplete image reconstructed by using the PAR. Therefore, a user may recognize a change in an HU value more quickly, and accurately determine a tomography start point desired by the user.

Figure 6:
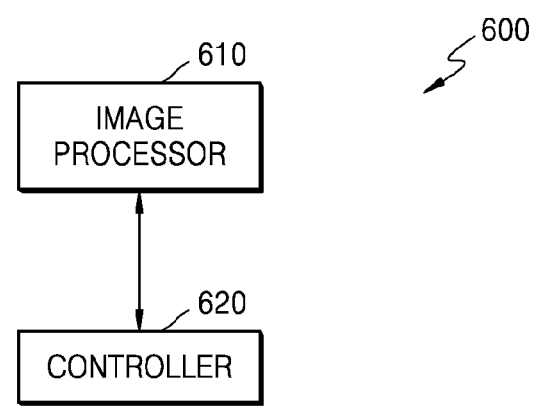
FIG. 6 is a block diagram illustrating a tomography apparatus according to an exemplary embodiment.

FIG. 6 is a block diagram illustrating a tomography apparatus 600 according to an exemplary embodiment.

Referring to FIG. 6, the tomography apparatus 600 according to the exemplary embodiment includes an image processor 610 and a controller 620. The tomography apparatus 600 denotes all electronic apparatuses that may perform tomography, and obtain, reconstruct, and/or display a cross-sectional image.

The tomography apparatus 600 may be included inside the CT system 100 described with reference to FIGS. 1 and 2. In this case, the image processor 610 and the controller 620 may equally correspond to the image processor 126 and the controller 118, respectively, illustrated in FIG. 2. Also, the tomography apparatus 600 may be included inside the medical apparatus 136 or the portable device 138 described with reference to FIG. 3, and connected with the CT system 100.

The tomography apparatus 600 is described below with reference to FIG. 5.

The image processor 610 performs tomography on an object, obtains raw data from various angle sections, and obtains a partial image corresponding to each of the angle sections by using the obtained raw data.

The tomography apparatus 600 according to the exemplary embodiment may obtain two or more partial images from two or more angle sections. A process in which the tomography apparatus 600 obtains two partial images from two angle sections is described below as an example.

The image processor 610 obtains a first image, which is a partial image, by using raw data obtained from a first angle section corresponding to a first point, and obtains a second image, which is a partial image, by using raw data obtained from a second angle section corresponding to a second point subsequent to the first point. Here, the second angle section may be a section that is continuous with the first angle section, or may be an angle section that is not continuous with the first angle section but adjacent to the first angle section. Also, the first angle section and the second angle section may have a value less than 180 degrees. The first image and the second image become incomplete images obtained by using the PAR.

Here, the first point corresponds to an obtaining point of raw data obtained for reconstructing the first image, and the second point corresponds to an obtaining point of raw data obtained for reconstructing the second image. For example, in the case of reconstructing the first image by using raw data obtained for a time section ranging from t1 to t2, the first point may become a point (t1+t2)/2, which is a middle of the time section ranging from t1 to t2. Also, in the case of reconstructing the second image by using raw data obtained for a time section ranging from t2 to t3, the second point may become a point (t2+t3)/2, which is a middle of the time section ranging from t2 to t3.

Also, the first image represents an object at the first point, and the second image represents the object at the second point.

A case where the first image is a partial image 510 reconstructed by using raw data obtained from the time section ranging from t1 to t2 or an angle section a1, and the second image is a partial image 520 reconstructed by using raw data obtained from the time section ranging from t2 to t3 or an angle section a2 is described below as an example. That is, a case where the second angle section a2 is an angle section that is continuously adjacent to the first angle section a1 is described as an example.

The controller 620 obtains first information representing a brightness change between a region of interest of the first image and a region of interest of the second image. Also, the controller 620 obtains second information representing a rate of change of an HU value between the first point and the second point based on the first information, and determines a tomography start point of an object based on the second information.

The controller 620 may compare the first image 510 with the second image 520 and obtain information representing a brightness change of a predetermined region inside the images. First, a region of interest may be set in the first image 510 and the second image 520. The region of interest of the first image 510 and the region of interest of the second image 520 are described below with reference to FIG. 7.

Figure 7:
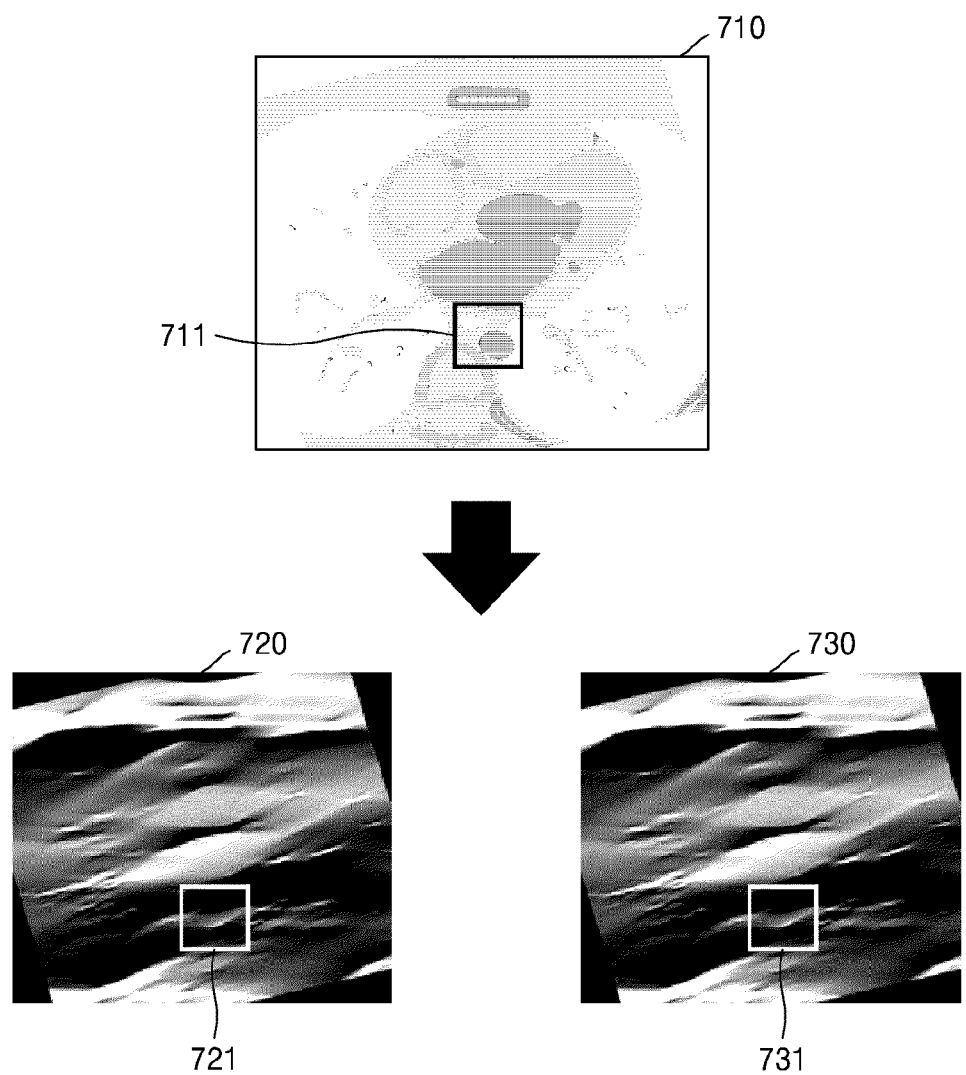
FIG. 7 is a diagram for explaining setting a region of interest in a partial image.

FIG. 7 is a diagram for explaining setting a region of interest in a partial image. That is, FIG. 7 is a diagram for explaining an operation of setting a region of interest in the first image 510 and the second image 520 which are partial images.

The tomography apparatus 600 according to an exemplary embodiment may perform tomography on an object to obtain raw data before injecting contrast media, and obtain an initial image by using the raw data. Since the obtained initial image is a complete image reconstructed by using the full reconstruction method or the half reconstruction method, a region of interest designating a predetermined location and a region inside the object may be easily set in the initial image. The tomography apparatus 600 may set a region of interest in the initial image via a user input device. Since the user input device is described below with reference to FIG. 11, a description thereof is omitted.

The tomography apparatus 600 may obtain partial images from various angle sections by using raw data. The obtained partial images are incomplete images reconstructed by using the PAR. Also, since partial images include only a portion of the surface of an object, it is difficult to accurately set a region of interest representing a predetermined location and a region of an object in a partial image. Therefore, it is possible to set a region of interest inside an initial image, which is a complete image, and set a region of interest in a partial image based on a location coordinate of the region of interest set in the initial image.

Specifically, it is possible to set the region of interest designating the same region of the object in the partial image by using coordinate information, size information, etc. of the region of interest set in the initial image. The region of interest of the partial image may correspond to the same location and the same area as those of the region of interest set in the initial region.

Referring to FIG. 7, a diagram shown in the upper side illustrates a region of interest 711 set in an initial image 710. Diagrams shown in the lower side illustrate regions of interest 721 and 731 set in partial images 720 and 730 different from each other based on the location of a region of interest set in an initial image. Since the partial images 720 and 730 are incomplete images, they do not entirely represent an object. Therefore, it is difficult for a user to intuitively set a region of interest in a partial image based on a shown portion as in the case of setting a region of interest in a complete image. Therefore, the user may set a region of interest in a partial image based on the location of a region of interest set in an initial image which is a complete image.

The partial image 720 represents the first image 720, and may equally correspond to the partial image 510 illustrated in FIG. 5. Also, the partial image 730 represents the second image 730, and may equally correspond to the partial image 520. Specifically, the first image 720 may be a partial image representing an object at a point (t1+t2)/2, which is the first point, described in FIG. 5, and the second image 730 may be a partial image representing the object at a point (t2+t3)/2, which is the second point, described in FIG. 5.

The controller 620 obtains first information representing a brightness change between a region of interest 721 set in the first image 720 and a region of interest 731 set in the second image 730. As described above, since the first image 720 and the second image 730 are images reconstructed by using raw data obtained from angle sections that are adjacent and continuous, or that are not continuous but close, they may image the same or similar region of an object. Therefore, it is possible to measure a change in a brightness value of images in the same or similar region of the object by comparing the first image 720 with the second image 730. Also, the first image 720 and the second image 730 are partial images, and images having high temporal resolution. Specifically, since the X-ray generator 106 performs tomography while rotating at a predetermined velocity, an angle value is in proportion to a time value, and when a value of a predetermined angle section is reduced, a time taken for obtaining raw data from the predetermined angle section is reduced. Therefore, in PAR, as an angle section used for reconstructing a partial image reduces, temporal resolution may increase. Therefore, the first image 720 and the second image 730, which are partial images, become images having high temporal resolution and are images in which movement artifacts nearly do not exist, and may become images accurately representing a portion of an object without blurring.

An object of a patient mostly includes a moving organ, a blood vessel continuously expanding or contracting, etc. Therefore, movement artifacts or blurring inevitably occurs in a cross-sectional image that has captured an image of a moving object. Therefore, temporal resolution should be increased to minimize movement artifacts or blurring, so that an image more clearly imaging an object may be obtained.

In an exemplary embodiment, a brightness change at a predetermined point inside an image may be accurately measured by comparing the first image 720 with the second image 730 more clearly imaging an object due to high temporal resolution.

Specifically, after contrast media are injected, as time elapses, a portion in which a contrast enhancement effect appears is displayed brightly, and an HU value appears large. Since the second point (for example, the point (t2+t3)/2 in FIG. 5) is a point subsequent to the first point (for example, the point (t1+t2)/2 in FIG. 5), a contrast enhancement effect in the second image may be greater than that in the first image, and the controller 620 may determine a difference in a brightness change between the first image 720 and the second image 730.

Here, a difference in brightness due to a contrast enhancement effect should be compared with respect to the same region of the first image 720 and the second image 730. Specifically, since a region which a user desires to observe is a region of interest (ROI) set in a cross-sectional image, a difference in a brightness change between regions of interest of the first image and the second image may be determined. When the brightness change of the first image 720 and the second image 730 is known, a change in an HU value corresponding to the brightness change may be known. Specifically, the brightness change and the change in the corresponding HU value between regions of interest of the first image 720 and the second image 730 may be obtained experimentally. The tomography apparatus 600 according to an exemplary embodiment may experimentally obtain a table mapping a brightness change of the same location between the first image 720 and the second image 730, which are partial images, to a change in an HU value, and store the table.

Also, the controller 620 may obtain second information representing a rate of change in an HU value between the first point and the second point based on the first information. Since the first image and the second image are partial images, an HU value in a region of interest of the first image and the second image may not be the same as an HU value in a complete image entirely representing an object. Therefore, the controller 620 may obtain the second information by correcting a difference between an HU value in a complete image and an HU value in a partial image.

Specifically, the tomography apparatus 600 may use first information representing a brightness change of a partial image and a lookup table including an HU value in a complete image corresponding to the first information. The lookup table may be obtained by experiment, and may change depending on an object to be measured, specification of a tomography apparatus, a manufacturer, etc.

Also, the controller 620 may determine a tomography start point of an object based on the second information. Since the tomography start point should be a point at which a high contrast enhancement effect is maintained, the tomography start point may be a point at which an HU value is equal to or greater than a predetermined threshold value. Also, the tomography start point may be a point at which an HU value reaches a target HU value received from a user.

Figure 8:
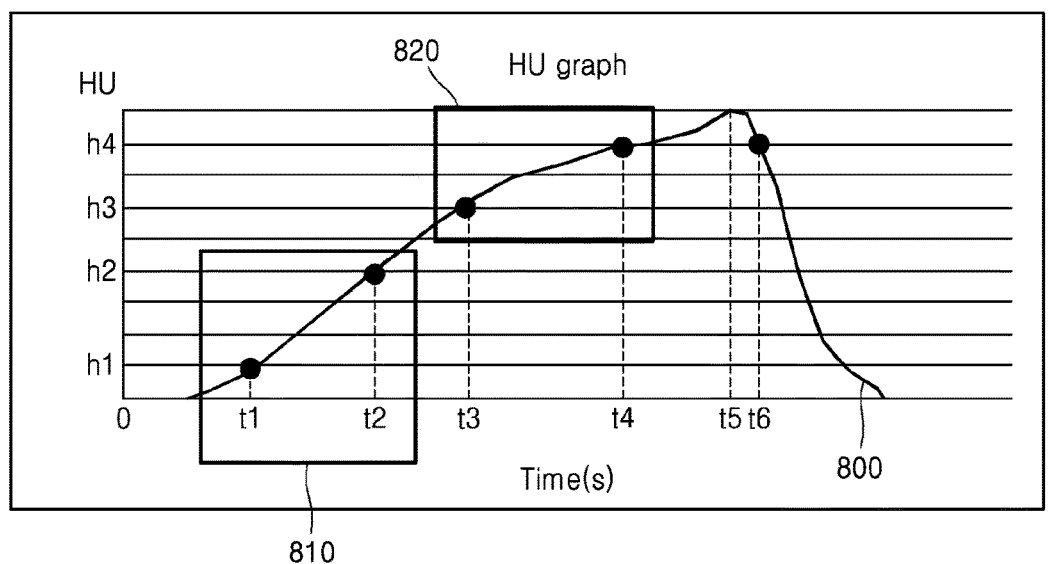
FIG. 8 is a graph illustrating a change of a Hounsfield unit (HU) value depending on time.

FIG. 8 is a graph 800 illustrating a change of an HU value depending on time. Specifically, FIG. 8 is the graph 800 illustrating a change of an HU value, which is the second information representing a rate of change of an HU value depending on time obtained based on the first information.

Referring to FIG. 8, HU values corresponding to points t1 and t2 may be represented as values h1 and h2, respectively. The values h1 and h2 corresponding to the points t1 and t2 may be known by using a lookup table, and a rate of change of an HU value in a section 810 ranging from t1 to t2 may be obtained via the HU values corresponding to the points t1 and t2. Likewise, HU values corresponding to points t3 and t4 may be represented as values h3 and h4, respectively, and a rate of change of an HU value in a section 820 ranging from t3 to t4 may be obtained via the HU values corresponding to the points t3 and t4.

A rate of change of an HU value may be expressed as a slope in the graph 800, a rate of change of an HU value in the section ranging from t1 to t2 may be represented by (h2−h1)/(t2−t1), and a rate of change of an HU value in the section ranging from t3 to t4 may be represented by (h4−h3)/(t4-t3). Therefore, the tomography apparatus 600 may predict an HU value at a predetermined point, and accurately determine a tomography start point desired by a user.

For example, depending on a contrast enhancement effect, assume that an HU value required for accurately reading an image in a cross-sectional image representing an object to which contrast media have been injected is a value h4 or more. The tomography apparatus 600 may specify a point at which an HU value is h4 or more as t4, and reconstruct a cross-sectional image by using raw data obtained from the specified point t4. Specifically, the tomography apparatus 600 may reconstruct a cross-sectional image by using raw data obtained during a time section between points t4 to t6, which is a section in which an HU value is h4 or more.

Figure 9:
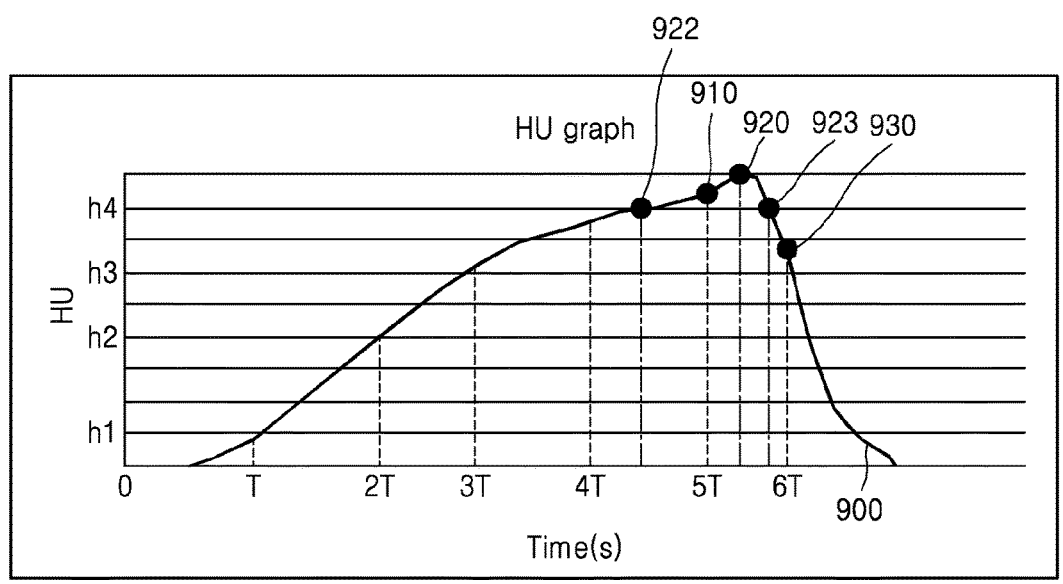
FIG. 9 is a graph for explaining a difference between methods of determining a tomography start point depending on a reconstruction method.

FIG. 9 is a diagram for explaining a graph comparing a method of determining a tomography start point by using the full reconstruction method or the half reconstruction method with a method of determining a tomography start point by using the PAR method.

First, a case of determining a tomography start point by using the full reconstruction method is described as an example. An HU value may be determined inside an image completely representing an object. Therefore, when a time taken for a gantry to rotate one time or more in order to reconstruct an image fully is expressed as one period in a tomography apparatus reconstructing a cross-sectional image by using the full reconstruction method, a user may determine a change of an HU value on a period basis. Referring to the graph of FIG. 9, when one period is represented as T, the user may determine a change of HU values at points T, 2T, and 3T. Therefore, it may be difficult to determine HU values at points between T and 2T, and between 2T and 3T. Here, a tomography start point may be a point 922 at which an HU value is a predetermined value or more.

However, when a rate of change in an HU value is obtained by using a partial image corresponding to an angle section of less than a half rotation, a change of an HU value may be determined on a shorter time basis. Also, an HU value at a specific point may be predicted by using a graph representing a change of an HU value depending on time. Therefore, referring to the graph of FIG. 9, the tomography apparatus 600 according to an exemplary embodiment may accurately determine a point 920 at which an HU value is maximized. Also, the tomography apparatus 600 according to an exemplary embodiment may accurately determine a time section ranging from a point 922 to a point 923, which is a time section having an HU value equal to or greater than a predetermined threshold value (for example, h4). Compared with this, in the case where an HU value may be determined on a period basis, HU values at points 910 and 930 are determined alone, and a point 920 at which an HU value is maximized or the time section ranging from the point 922 to the point 923 in which an HU value is equal to or greater than the predetermined threshold value may not be accurately specified.

Also, the controller 620 may control to automatically extract a start point of the tomography based on the second information, and to reconstruct a cross-sectional image by using raw data obtained from the extracted point.

Also, the controller 620 may control to automatically extract a raw data obtaining section for reconstructing a cross-sectional image based on the second information, and to reconstruct a cross-sectional image by using raw data obtained from the extracted section. Specifically, the controller 620 may control to reconstruct a cross-sectional image by using raw data obtained from a range over t4 to t6 illustrated in FIG. 8.

Also, the controller 620 may control to display the second information via a display. Also, the controller 620 may control to display a user interface screen that displays a tomography start point in the second information via the display.

Figure 10:
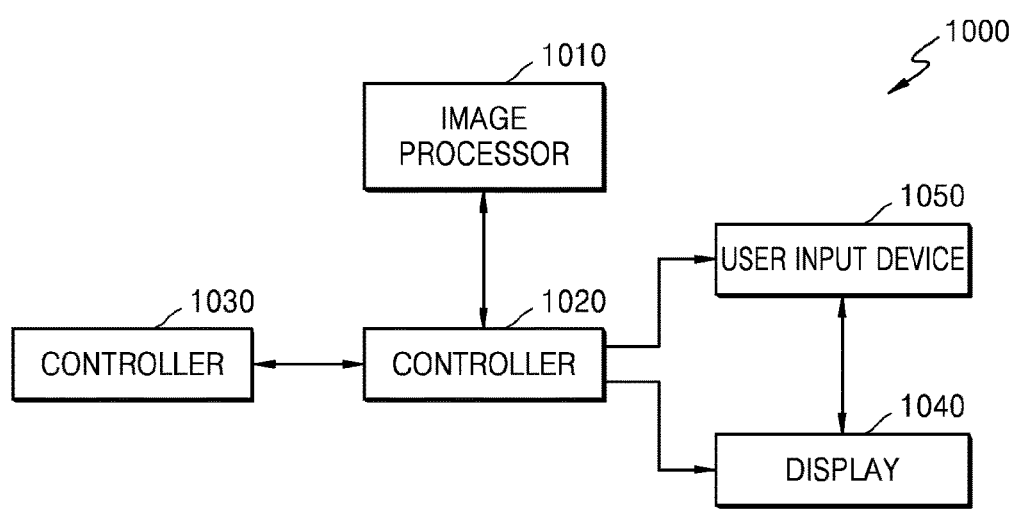
FIG. 10 is a block diagram illustrating a tomography apparatus according to an exemplary embodiment.

FIG. 10 is a block diagram illustrating a tomography apparatus 1000 according to an exemplary embodiment. In FIG. 10, since an image processor 1010 and a controller 1020 equally correspond to the image processor 610 and the controller 620 of FIG. 6, repeated descriptions thereof are omitted.

Referring to FIG. 10, the tomography apparatus 1000 includes the image processor 1010 and the controller 1020. Also, the tomography apparatus 1000 may further include at least one of a user input device 1050, a display 1040, and a storage device 1030. Since the user input device 1050, the display 1040, and the storage device 1030 included in the tomography apparatus 1000 are the same as the input unit 128, the display 130, and the storage device 124 of the CT system 100 illustrated in FIG. 2, repeated descriptions thereof are omitted.

The storage device 1030 may store a lookup table and data obtained from the tomography. Specifically, the storage device 1030 may store at least one of projection data and a sinogram, which are raw data. The storage device 1030 may store various kinds of data, a program, etc. required for reconstructing a cross-sectional image, and store a finally reconstructed cross-sectional image. Also, the storage device 1030 may store data required for obtaining the first information and the obtained first information, and data required for obtaining the second information and the obtained second information. Also, the storage device 1030 may store data required for determining a tomography start point and the determined tomography start point.

The display 1040 may display a user interface screen required for performing the tomography, or a reconstructed cross-sectional image, etc. Also, the display may display a user interface including a graph representing a change of an HU value depending on time.

The user input device 1050 may generate and output a user interface screen for receiving a predetermined command or data from a user. Specifically, the user input device 1050 may receive a target HU value from the user in determining a tomography start point.

The user input device 1050 may include a mouse, a keyboard, or an input unit including hard keys for receiving predetermined data. A user may input predetermined data or a command by manipulating at least one of the mouse, the keyboard, or other input units included in the user input device 1050.

Also, the user input device 1050 may include a touchpad. Specifically, the user input device 1050 includes a touchpad coupled to a display panel included in the display 1040, and outputs a user interface screen on the display panel. Also, when a predetermined command is input via the user interface screen, the touchpad may recognize the predetermined command input by a user by detecting the predetermined command.

Specifically, in the case where the user input device 1050 includes the touchpad, when a user touches a predetermined point of the user interface screen, the user input device 1050 detects the touched point. Also, the user input device 1050 may transmit detected information to the controller 1020. Then, the controller 1020 may recognize the user's request or a command corresponding to a menu displayed at the detected point, and perform a tomography operation by reflecting the recognized request or command.

Figure 11:
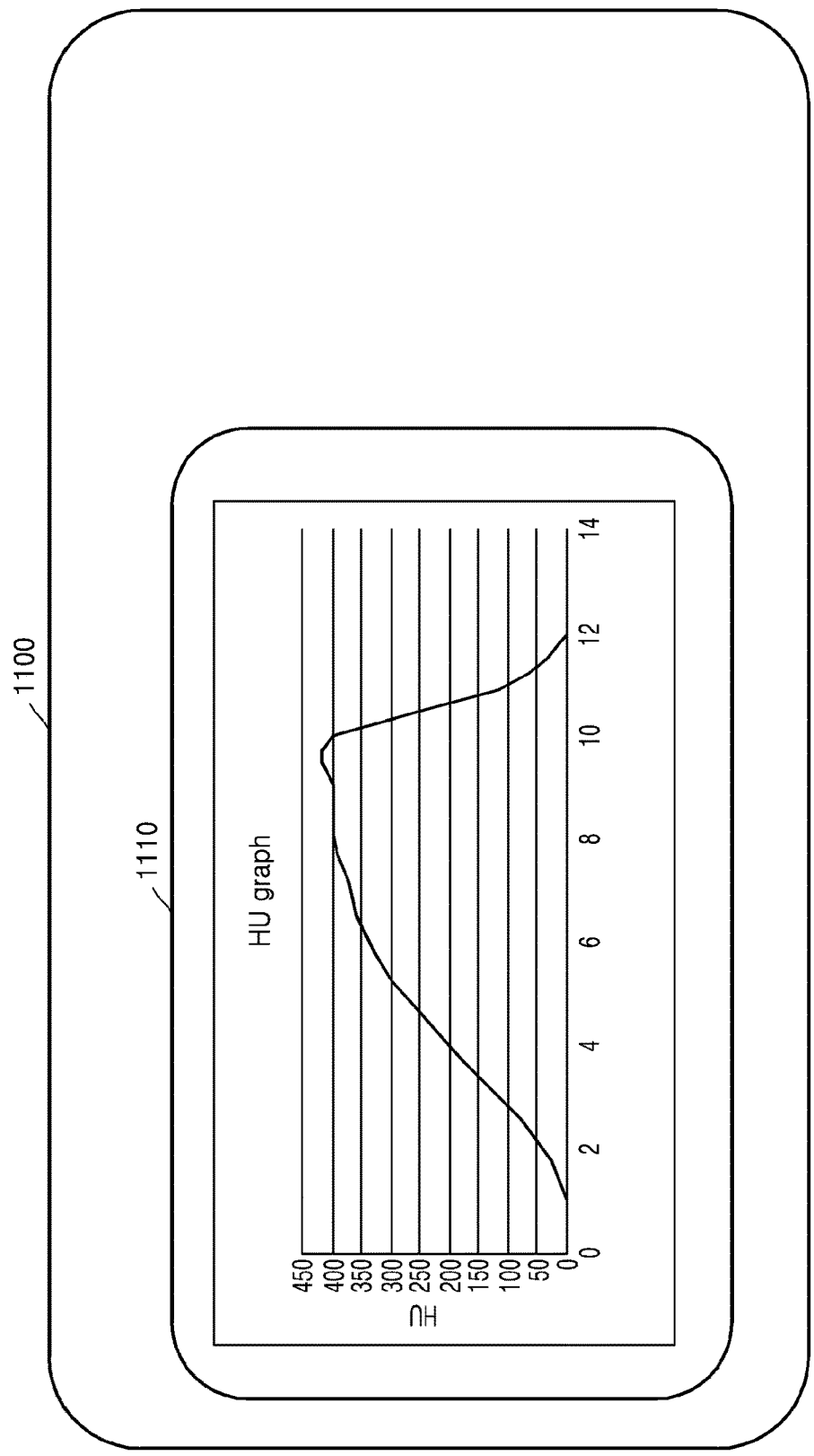
FIG. 11 is a diagram illustrating a user interface screen including a graph representing a change of an HU value depending on time in a tomography apparatus according to an exemplary embodiment.

FIG. 11 is a diagram illustrating a user interface screen including a graph representing a change of an HU value depending on time in a tomography apparatus 1000 according to an exemplary embodiment.

Referring to FIG. 11, the display 1040 may display a user interface screen 1100 including a graph 1110 representing a change of an HU value depending on time. Also, the user interface screen 1100 may display the graph 1110 and a tomography start point determined by the controller 1020 together. Also, the user interface screen 1100 may display the graph 1110 and a target HU value input from the user input device 1050 together.

Figure 12:
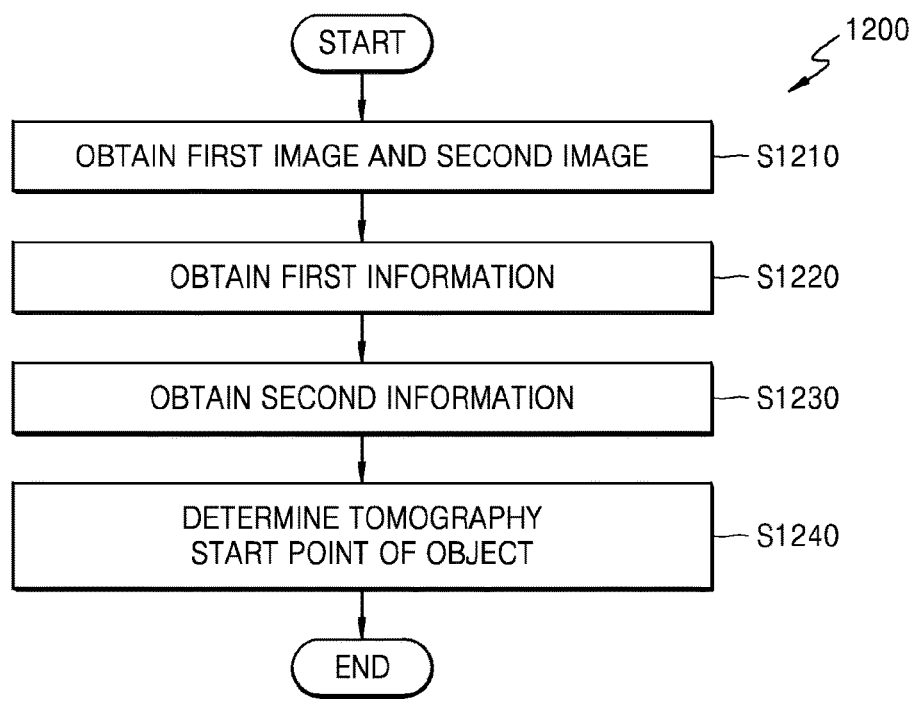
FIG. 12 is a flowchart illustrating a tomography method according to an exemplary embodiment.

FIG. 12 is a flowchart illustrating a tomography method 1200 according to an embodiment. An operation configuration of the tomography method 1200 according to an exemplary embodiment is the same as the operation configuration of the tomography apparatuses 600 and 1000 according to the exemplary embodiments described with reference to FIGS. 1 to 11. Therefore, in describing the tomography method, descriptions previously set forth with respect to FIGS. 1 to 11 are not repeated.

Referring to FIG. 12, the tomography method 1200 according to the exemplary embodiment obtains a partial image by performing tomography on an object in operation S1210. Specifically, the tomography is performed on an object. A first image, which is a partial image, is obtained by using raw data obtained from a first angle section corresponding to a first point, and a second image, which is a partial image, is obtained by using raw data obtained from a second angle section corresponding to a second point. Operation S1210 may be performed by the image processor 1010 of the tomography apparatus 1000 according to an exemplary embodiment. Here, the second angle section may be a section that is continuous with the first angle section, or may be an angle section that is not continuous with the first angle section but adjacent to the first angle section. Also, the first angle section and the second angle section may have a value less than 180 degrees.

In operation S1220, first information representing a brightness change between a region of interest of the first image and a region of interest of the second image is obtained. Operation S1220 may be performed by the controller 1020 of the tomography apparatus 1000.

After contrast media are injected, a portion in which a contrast enhancement effect appears large is expressed more brightly, and the first information may be information representing a brightness change when a contrast enhancement effect increases in a region of interest.

In operation S1230, second information representing a rate of change of an HU value between the first point and the second point is obtained based on the first information. Operation S1230 may be performed by the controller 1020 of the tomography apparatus 1000. Here, the second information may be obtained by using the first information and a lookup table including an HU value corresponding to the first information.

In operation S1240, a tomography start point of an object is determined based on the second information. The tomography start point may be a point at which an HU value reaches a target HV value set by a user, or may be a point at which an HU value is equal to or greater than a predetermined threshold value. Operation S1240 may be performed by the controller 1020 of the tomography apparatus 1000.

As described above, the tomography apparatus and method according to an exemplary embodiment may predict a change in an HU value depending on time by using a partial image corresponding to various angle sections, and predict an accurate tomography start point desired by a user.

Tomography captures an image of an object by radiating an X-ray to a patient. However, since an X-ray used for tomography is a radioactive material, the X-ray is harmful to a human body. Therefore, a user needs to reduce a dose of radiation exposed to a patient including an object during an X-ray examination.

The tomography apparatus and method according to an exemplary embodiment may predict a change in an HU value by using even a small number of times of tomography compared with a conventional method, and consequently, a dose of a patient's radiation exposure may be reduced. Also, the tomography apparatus and method according to an exemplary embodiment may reduce an amount of unnecessary contrast media injected to a patient by predicting an accurate tomography start point.

The exemplary embodiments may be written as computer programs and may be implemented in general-use digital computers that execute the programs using a non-transitory computer-readable recording medium.

Examples of the non-transitory computer-readable recording medium include magnetic storage media (e.g., ROM, floppy disks, hard disks, etc.), optical recording media (e.g., CD-ROMs, or DVDs), etc.

While one or more exemplary embodiments have been described with reference to the figures, it will be understood by those of ordinary skill in the art that various changes in form and details may be made therein without departing from the spirit and scope of the exemplary embodiments as defined by the following claims.

What is claimed is:

1. A tomography apparatus comprising:
    an image processor configured to perform tomography on an object using an imaging device which rotates around the object along a rotation path, to thereby obtain a first image, which is a partial image of the object, by using data obtained from a first angle section of the rotation path, the first angle section corresponding to a first point, and to obtain a second image, which is a partial image of the object, by using data obtained from a second angle section of the rotation path, the second angle section corresponding to a second point subsequent to the first point along the rotation path; and
    a controller configured to obtain first information representing a brightness change between a region of interest of the first image and a region of interest of the second image designating a same location of the object, to obtain second information representing a rate of change in a Hounsfield unit (HU) value between the first point and the second point based on the first information, and to determine a tomography start point of the object based on the second information.

2. The tomography apparatus of claim 1, wherein the first angle section is less than 180 degrees and the second angle section is less than 180 degrees.

3. The tomography apparatus of claim 1, wherein the image processor is configured to reconstruct the first image, which is an incomplete image, by using raw data obtained from the first angle section of the rotation path, and reconstruct the second image, which is an incomplete image, by using raw data obtained from the second angle section of the rotation path.

4. The tomography apparatus of claim 1, wherein the controller is configured to predict a time required for reaching a target HU value based on the second information, and determine the tomography start point based on the predicted time.

5. The tomography apparatus of claim 4, further comprising:
a user input device configured to receive the target HU value from a user.

6. The tomography apparatus of claim 1, wherein the controller is configured to determine a point at which the HU value is equal to or greater than a threshold value as the tomography start point based on the second information.

7. The tomography apparatus of claim 1, wherein the controller is configured to obtain the second information by mapping the first information to a rate of change of a HU value corresponding to the first information.

8. The tomography apparatus of claim 7, further comprising:
a storage device configured to store the first information and a lookup table including the rate of change of a HU value corresponding to the first information,
wherein the controller is configured to map the first information to the rate of change of a HU value corresponding to the first information by using the lookup table stored in the storage device.

9. The tomography apparatus of claim 1, further comprising:
a display configured to display a user interface screen comprising a graph representing the rate of change in the HU value over time.

10. The tomography apparatus of claim 1, wherein the image processor is configured to obtain an initial image reconstructed by using raw data obtained from the tomography, and set a region of interest in the obtained initial image.

11. The tomography apparatus of claim 10, wherein the image processor is configured to set the region of interest of the first image and the region of interest of the second image based on a location of the region of interest set in the obtained initial image.

12. A tomography apparatus comprising:
an image processor configured to perform tomography on an object using an imaging device which rotates around the object along a rotation path to obtain a plurality of partial images by using data obtained from a plurality of angle sections of the rotation path, the plurality of angle sections respectively corresponding to a plurality of successive points; and
a controller configured to set a region of interest designating a same location of the object in each of the plurality of partial images, to obtain first information representing a change in brightness between the regions of interest of two partial images corresponding to the plurality of successive points from among the plurality of partial images, to obtain second information representing a rate of change in a Hounsfield unit (HU) value in a time section comprising two adjacent points based on the first information, and to determine a tomography start point of the object based on the second information.

13. A tomography method comprising:
performing tomography on an object using an imaging device which rotates around the object along a rotation path;
obtaining, by the performing of the tomography, a first image, which is a partial image of the object, by using data obtained from a first angle section of the rotation path, the first angle section corresponding to a first point, and obtaining, by the performing of the tomography, a second image, which is a partial image of the object, by using data obtained from a second angle section of the rotation path, the second angle section corresponding to a second point subsequent to the first point along the rotation path;
obtaining first information representing a brightness change between a region of interest of the first image and a region of interest of the second image designating a same location of the object;
obtaining second information representing a rate of change in a Hounsfield unit (HU) value between the first point and the second point based on the first information; and
determining a tomography start point of the object based on the second information.

14. The tomography method of claim 13, wherein the first angle section is less than 180 degrees and the second angle section is less than 180 degrees.

15. The tomography method of claim 13, wherein the obtaining of the first image and the second image comprises:
reconstructing the first image, which is an incomplete image, by using raw data obtained from the first angle section of the rotation path, and
reconstructing the second image, which is an incomplete image, by using raw data obtained from the second angle section of the rotation path.

16. The tomography method of claim 13, wherein the determining of the tomography start point comprises:
predicting a time required to reach a target HU value based on the second information; and
determining the tomography start point based on the predicted time.

17. The tomography method of claim 16, further comprising:
receiving the target HU value from a user.

18. The tomography method of claim 13, wherein the determining of the tomography start point comprises:
determining a point at which the HU value is equal to or greater than a threshold value as the tomography start point based on the second information.

19. The tomography method of claim 13, wherein the obtaining of the second information comprises:
mapping the first information to a rate of change of a HU value corresponding to the first information.

20. The tomography method of claim 19, wherein the mapping comprises:
mapping the first information to the rate of change of a HU value corresponding to the first information by using the first information and a lookup table comprising the rate of change of a HU value corresponding to the first information.

* * * * *